US006555361B1

(12) United States Patent
Lyman et al.

(10) Patent No.: US 6,555,361 B1
(45) Date of Patent: Apr. 29, 2003

(54) HYBRIDIZATION CHAMBER FOR HIGH DENSITY NUCLEIC ACID ARRAYS

(75) Inventors: George F. Lyman, Kennebunk Port, ME (US); Vic E. Myer, Arlington, MA (US); Christopher J. Wilson, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/534,948

(22) Filed: Mar. 24, 2000

Related U.S. Application Data

(60) Provisional application No. 60/125,820, filed on Mar. 24, 1999.

(51) Int. Cl.$^{7}$ .............................................. C12M 1/34

(52) U.S. Cl. ................................ 435/287.2; 435/288.3; 435/288.4

(58) Field of Search ...................... 435/6, 285.1, 287.2, 435/288.3, 288.4

(56) References Cited

U.S. PATENT DOCUMENTS

| | | | | |
|---|---|---|---|---|
| 5,360,741 A | | 11/1994 | Hunnell | 435/290 |
| 5,675,700 A | * | 10/1997 | Atwood et al. | 219/521 |
| 5,681,741 A | * | 10/1997 | Atwood et al. | 422/102 |
| 6,127,188 A | * | 10/2000 | Sullivan | 424/78.24 |
| 6,132,682 A | * | 10/2000 | Christner et al. | 422/58 |
| 6,258,593 B1 | * | 7/2001 | Schembri et al. | 435/287.2 |
| 6,261,523 B1 | * | 7/2001 | Schembri | 220/789 |

FOREIGN PATENT DOCUMENTS

| | | | |
|---|---|---|---|
| WO | WO 95/21909 | 8/1995 | C12M/1/38 |
| WO | WO 97/12063 | 4/1997 | C12Q/1/68 |

* cited by examiner

*Primary Examiner*—David A. Redding
(74) *Attorney, Agent, or Firm*—Thomas R. Beall

(57) ABSTRACT

The present invention provides a hybridization chamber that contains a built-in mechanism for saturating the air within the chamber when sealed thereby preventing drying of the liquid sample. The hybridization chamber is defined by matching top and bottom clam-shell like halves that, when brought together, are sealed by an o-ring and clamping device. The chamber is equipped with a liquid reservoir, the liquid from which will serve to saturate the volume of air sealed within the hybridization chamber. A saturated atmosphere within the chamber prevents evaporation of the sample.

7 Claims, 4 Drawing Sheets

HYBRIDIZATION CHAMBER FOR HIGH DENSITY NUCLEIC ACID ARRAYS

This application claims the benefit of Provisional Application No. 60/125,820 filed on Mar. 24, 1999.

FIELD OF THE INVENTION

This invention relates to a DNA hybridization incubation chamber for use in performing DNA hybridization assays.

BACKGROUND OF THE INVENTION

High density arrays are new tools used by drug researchers and geneticists which provide information on the expression of genes from particular cells. A high density array typically comprises between 5,000 and 50,000 probes in the form of DNA strands, each of known and different sequence, arranged in a determined pattern on a substrate. The substrate may be any size but typically takes the form of a 1×3 inch glass microscope slide.

The arrays are used to determine whether target sequences interact or hybridize with any of the probes on the array. After exposing the array to target sequences under selected test conditions, scanning devices can examine each location in the array and determine whether a target molecule has hybridized with the probe at that location. DNA arrays can be used to study which genes are "turned on" or up regulated and which genes are "turned off" or down regulated. So for example, a researcher can compare a normal colon cell with a malignant colon cell and thereby determine which genes are being expressed or not expressed only in the aberrant cell. The regulation of these genes serves as key targets for drug therapy.

Hybridization is a hydrogen bonding interaction between two nucleic acid strands that obey the Watson-Crick complementary rules. All other base pairs are mismatches that destabilize hybrids. Since a single mismatch decreases the melting temperature of a hybrid by up to 10 degrees C., conditions can be found at which only perfect hybrids can survive. Hybridization comprises contacting the strands, one of which is immobilized on the substrate and the other which usually bears a radioactive, chemoluminescent or fluorescent label, and then separating the resulting hybrids from the unreacted labeled strands by washing the support. Hybrids are recognized by detecting the label bound to the surface of the support.

In performing the hybridization, depending on reagent (buffer) compositions employed, and the similarity of the probe and target molecules, the temperature employed may vary from about ambient temperature to about 70° C. As described, temperature is used as a process variable in altering the hybridization stringency. Typically, nucleic acid and protein hybridizations are carried out in a closed container in a constant temperature environment for extended periods of time, e.g., 10–18 hours.

Since the hybridization assays require tight temperature control and a controlled environment, researchers use an enclosed system, often referred to as a hybridization chamber, in order to perform hybridization assay. The standard hybridization chamber consists of a plastic (typically polypropylene) two-piece construction. A base portion and a top portion join together to define an internal sealed chamber. The chamber is environmentally sealed by a rubber o-ring gasket assembly which both prevents ambient moisture or air from entering the chamber, as well as the escape of any liquid or vapor from the sample itself out of the chamber. The unit is completely sealed by the use of an o ring and external clamps.

The substrate, which contains the tethered array of probe nucleotides, is placed in the chamber. A small amount or minimal amount buffer solution containing the target probes is deposited on the array and is spread and covered with a cover-slip. The chamber is closed and sealed with the clamp mechanism, and the entire chamber is introduced into a temperature controlled environment in the form of a water bath, conventional oven, or hybridization incubator for example.

It has been discovered that incubating samples in the standard hybridization chamber at elevated temperature causes the sample at the edges of the cover-slip to evaporate into the cavity of the chamber. This evaporation causes the sample to dry out around the edges of the cover-slip. In turn, it has been found that hybridization either does not occur in these dried out areas, or is severely compromised.

By providing a liquid filled reservoir within the sealed environment of the hybridization chamber, the present invention solves the problem of excessive drying of the sample. The liquid in the reservoir evaporates into the environment of the sealed chamber thereby saturating the air and thus preventing the drying phenomenon around the edges of the cover-slip.

SUMMARY OF THE INVENTION

The present invention provides a hybridization chamber that contains a built-in mechanism for saturating the air within the chamber when sealed thereby preventing drying of the liquid sample. The hybridization chamber is defined by matching top and bottom clam-shell like halves that, when brought together, are sealed by an o-ring and clamping device. The chamber is equipped with a liquid reservoir, the liquid from which will serve to saturate the volume of air sealed within the hybridization chamber. A saturated atmosphere within the chamber prevents evaporation of the sample.

DESCRIPTION OF THE INVENTION

Figure 1:
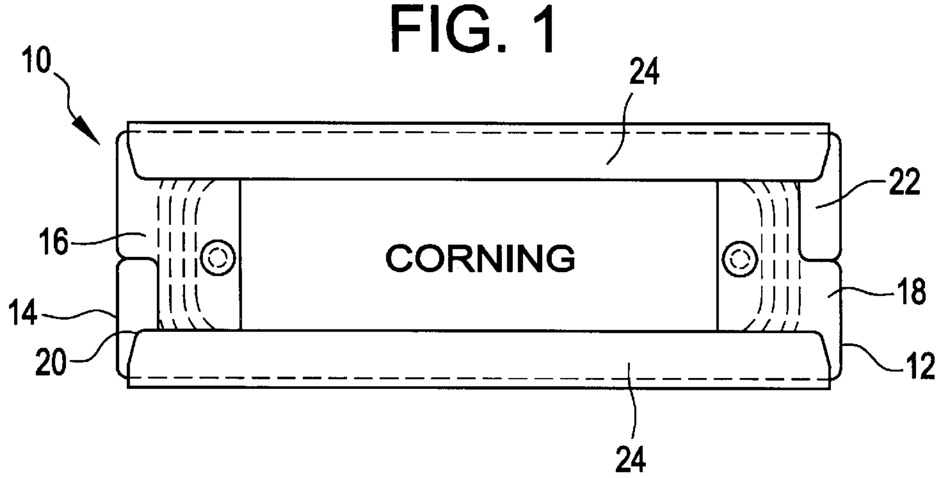
FIG. 1 is a front elevation view of the fully assembled hybridization chamber of the present invention.

The hybridization chamber 10 of the present invention is displayed in FIG. 1. Two clam-shell halves, a base or bottom portion 14 and a top portion 12, fittingly engage. Each clam-shell piece is equipped with alternate tabs that allow the clam-shell portions to be separated manually. For example, the top portion 12 has tabs 16, 18. the base portion 14 has tabs 20,22. The two clam-shell halves are held together by clamps 24 that are sized to engage the ends of the clam-shell portions by compression fit on the o ring. The clam-shell portions together define an interior chamber that is sealed from the external environment by the o ring.

Figure 2:
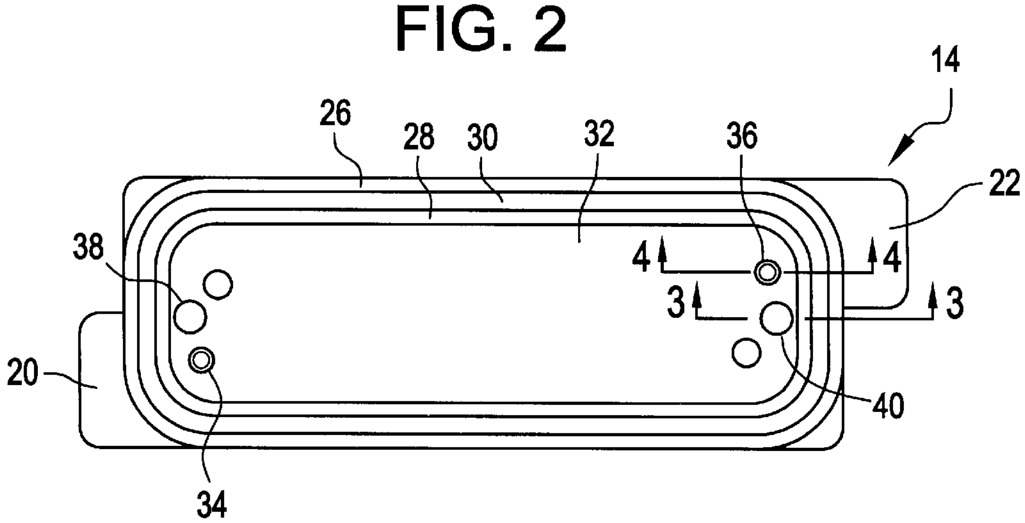
FIG. 2 is a front elevation view of the base portion of the hybridization chamber.

FIG. 2 is an elevation view of the base portion 14 having tabs 20,22. The base portion 14 is equipped with two raised oval rings 26, 28 that together define a groove 30. The groove 30 is sized to receive a rubber o-ring whose thickness will preferably exceed the height of the raised rings 26, 28. The rubber from which the o ring is made must have the proper durometer over the entire temperature range in order to keep the seal integral. Further, the interior most of the raised rings 28 defines a contained region 32 that is sized to receive a glass microscope slide and forms the floor of the interior chamber. Two posts 34,36 are located within the contained region. These posts engage corresponding depressions in the top portion of the hybridization chamber. The posts also serve to center a slide that is inserted into the chamber. The posts hold the slide in place and limit any movement of the slide itself within the chamber. Further, two reservoirs or wells 38,40 are molded into the contained region 32 such that they are depressed from the surface of the contained region. The wells can contain a small volume of liquid that when allowed to evaporate, will ensure a saturated environment within the interior chamber. It is important that the liquid that fills the wells not be allowed to wick out of the wells. The wells may be textured to increase surface area and surface tension thereby helping retain the liquid.

Another way to retain liquid within the well and minimize potential crosstalk is to insert a material that will absorb the liquid, but still allow it to evaporate. For example, the well may be filled with a bilayer laminate of a cellulosic material or hydrophilic synthetic polymer combined with a microporous polyolefin whereby the microporous polyolefin forms topmost layer. The microporous material will allow liquid to enter, but only escape by vapor. It may be conceived that the membrane laminate material need not be disposed in the well at all. As long as liquid is fully retained, a piece of the material may be inserted within the chamber and thereby perform the function of saturating the interior environment.

The wells may take any shape or form that is capable of containing liquid and may occupy any location within the hybridization chamber itself. For example, the wells may be elongated slits, rectangular, square, oval, etc. There may be any number of wells which may be depressed from the surface of the contained region, or alternatively rise above the surface. Ideally, the cumulative volume of the wells will be sufficient to fully saturate the environment within the chamber. The well may be covered by a film with a small slit in order to prevent liquid from escaping except as a vapor.

Figure 3:
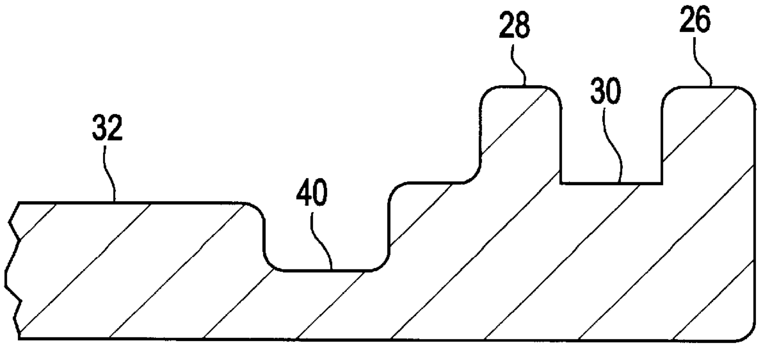
FIG. 3 is a partial cross-section view of the base portion along section line 3—3 of FIG. 2.

FIG. 3 is a partial cross-section taken along line 3—3 of FIG. 2. Groove 30 is defined by raised rings 26,28. Well 40 is molded into the surface of the contained region 32.

Figure 4:
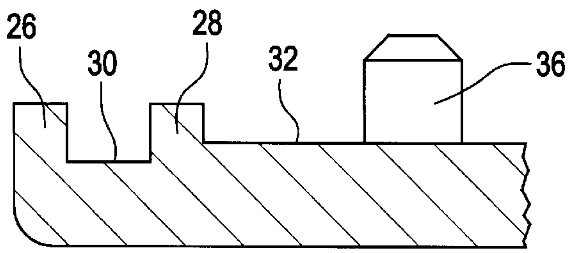
FIG. 4 is a partial cross-section view of the base portion along section line 4—4 of FIG. 2.

FIG. 4 is a partial cross-section taken along line 4—4 of FIG. 2. Groove 30 is defined by raised rings 26,28. Post 36 rises from the surface of the contained region 32. Groove 30 is sized to receive a rubber o-ring.

Figure 5:
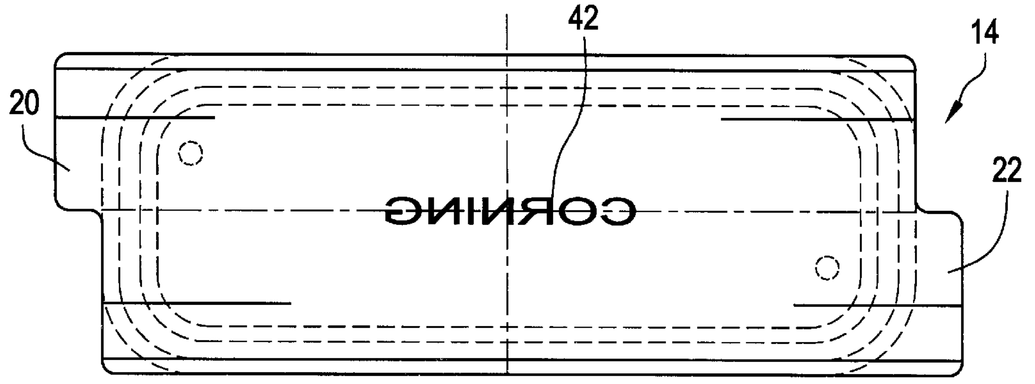
FIG. 5 is a back elevation view of the base portion of the hybridization chamber.

FIG. 5 is an elevation view of the flat back of the base portion 14 clam-shell half drawing tabs 20,22. Corporate insignia 42 may be molded into the back surface.

Figure 6:
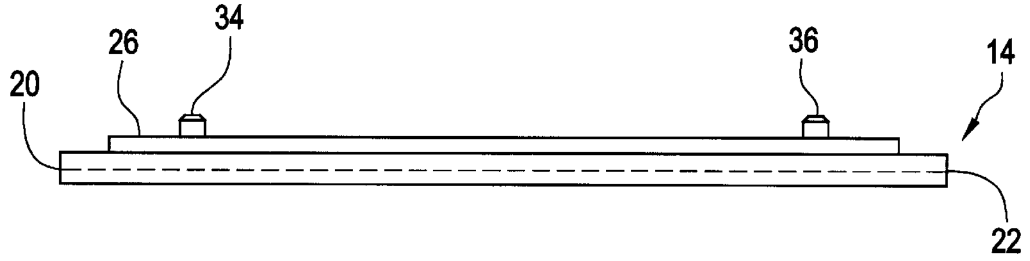
FIG. 6 is a side view of the base portion of the hybridization chamber.

FIG. 6 is a size view of the base portion 14 having tabs 20,22, raised ring 26, and posts 34,36. The clam-shell halves are preferably molded from a thermoplastic, and more preferably polypropylene, but may be constructed from any variety of polymers and plastics or even inorganic materials. Generally, the material from which the hybridization chamber is fabricated will be selected so as to provide maximum resistance to the full range of conditions to which the device will be exposed, e.g. extremes in temperature, salt, pH, application of electric fields, etc.

Figure 7:
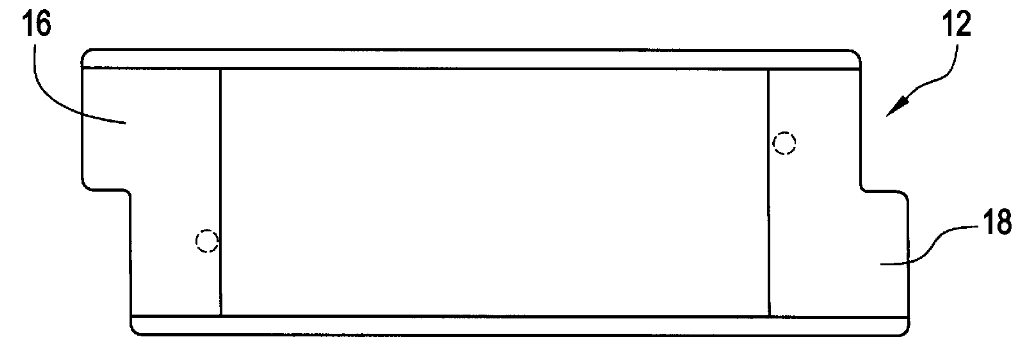
FIG. 7 is a front elevation view of the top portion of the hybridization chamber.

FIG. 7 is a front elevation view of the top portion 12 of the hybridization chamber having tabs 16,18.

Figure 8:
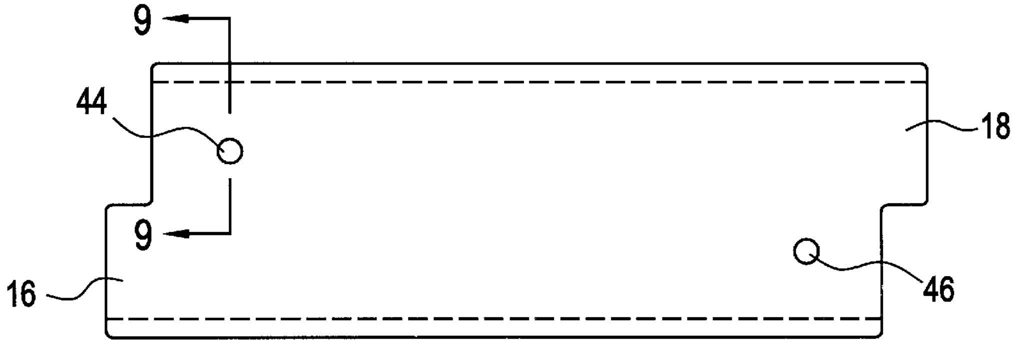
FIG. 8 is a back elevation view of the top portion of they hybridization chamber.

FIG. 8 is an underneath view of the top portion of the hybridization chamber having tabs 16,18. Depressed areas 44,46 are sized to engage respective posts from the base portion. The remainder of the top portion comprises a substantially flat surface.

Figure 9:
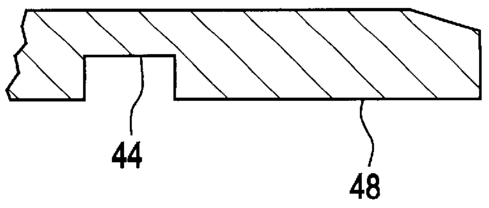
FIG. 9 is a partial cross-section view of the top portion along section line 9–9 of FIG. 8.

FIG. 9 is a partial cross-section taken along the line 9—9 of FIG. 8. Depressed area 44 is sized to fittingly engage a respective post from the base portion. The engagement of the posts and depressed areas of respective clam-shell halves ensure that the ports remain fixed together and serves to eliminate any lateral slipping between parts. An o-ring from the base portion will engage the surface 48 of the top portion, that when clamped together, will create an air and liquid tight seal.

Figure 10:
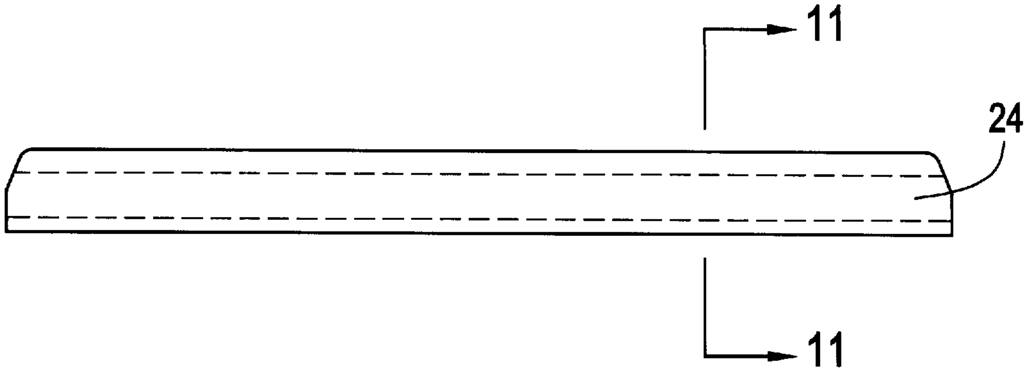
FIG. 10 is a side view of a clamp used to seal together the top and base portions of the hybridization chamber.
Figure 11:
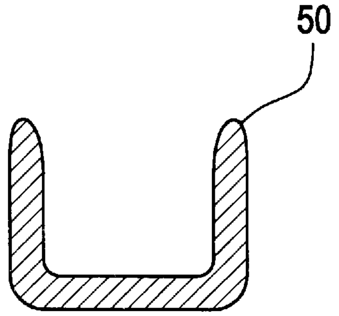
FIG. 11 is a section view of the clamp along section lines 11–11 of FIG. 10.

FIG. 10 is a side view of the clamp 24 that engages the length of the matched clamshell halves. FIG. 11 is a cross-section view along the line 11—11 of FIG. 10. The ends 50 of the clamp are preferably beveled in order to facilitate engagement of the parts. The clamps are preferably stainless steel, but also may be made from any suitable material. The clamps may also take the form of any shape that will effectively hold the clam-shell halves together by applying appropriate pressure.

In practical use, one places liquid, preferably water, in the wells of the base portion which is fitted with an o-ring. An array of DNA sequences immobilized on a glass slide is placed onto the contained region of the base portion, held in place between the raised posts. The posts are slightly offset from the wells thereby preventing the slide from ever contacting the wells themselves, thus eliminating the danger of crosstalk between the slide and the liquid retained in the wells. Next, the liquid sample to be tested is deposited onto the slide surface and a cover slip is placed over the slide. The top portion of the clam-shell is placed over the base portion such that the posts from the base portion engage the depressions in the top portion. Clamps are fitted onto the opposing lengths of the assembly in order to secure and seal the device. The device is then ready to be inserted into a controlled environment for hybridization. Typical sample volumes are between 5–15 microliters, a typical cover slip is approximately 20 mm×60 mm, and the incubation conditions are typically between 65–75 degrees C.

EXAMPLE

In a preferred embodiment, the clam-shell halves are each 4.465 inches long from tab end to tab end, and 1.496 inches wide. The bottom portion and top portion are each 0.120 inches thick. The raised rings that extend from the surface of the bottom portion rise 0.06 inches from the surface, are 0.07 inches wide, and are 0.1 inch apart. The posts are 0.125 inches in diameter and rise 0.13 inches above the surface. The wells are 0.12 inches in diameter and 0.06 inches deep. The depressions in the top portion are 0.125 inches in diameter and 0.06 inches deep. The clamps are 4.340 inches long 0.44 inches wide and 0.36 inches high. The width of the internal section of the clamp, which contacts the chamber ends, is 0.318 inches. The cross sectional diameter of the o ring (50 Duro BUNA-N; Apple Rubber Products, stock # AS568-149), which fully occupies the groove formed between the raised rings, is 0.103 inches, and the circumferential length of the ring is 2.8 inches.

Although the invention has been described in detail for the purpose of illustration, it is understood that such detail is solely for that purpose and variations can be made therein by those skilled in the art without departing from the spirit and scope of the invention which is defined by the following claims.

We claim:

1. A device for use in performing hybridization assays comprising:

a) a body having a chamber disposed therein including a chamber floor defined by a contained region for holding a liquid sample; and b) at least one well positioned within said chamber, the well adapted to retain liquid separately from said contained region and to allow controlled evaporation from the well;

whereby said chamber is capable of being hermetically sealed from an external environment.

2. The device of claim 1 wherein said chamber has a high density array disposed therein, said high density array including a substrate having a plurality of positionally distinct nucleotide probes immobilized to a surface of said substrate.

3. The device of claim 1 further comprising alternate mating base and top portions that collectively define said chamber.

4. The device of claim 3 wherein said at least one well is integrally molded into said base portion.

5. The device of claim 4 wherein said base portion further comprises a surface, a groove defined by a pair of rings that rise from said surface circumscribing said surface, and an o-ring disposed in said groove.

6. The device of claim 5 wherein said base portion further comprises at least one post rising from said surface of said base portion and at least one corresponding depression located within a surface of said top portion whereby said posts of said bottom portion fittingly engage said depressions of said top portion and whereby said o-ring engages said surface of said top portion.

7. The device of claim 1 werein said well has disposed within it a microporous membrane material which will allow liquid to enter said well, but allow liquid to escape said well only in vapor form.

* * * * *